United States Patent [19]
Andelman

[11] Patent Number: 5,748,437
[45] Date of Patent: May 5, 1998

[54] FLUID SEPARATION SYSTEM WITH FLOW-THROUGH CAPACITOR

[76] Inventor: Marc D. Andelman, 3 Fenimore Rd., Worcester, Mass. 01609

[21] Appl. No.: 653,832

[22] Filed: May 28, 1996

Related U.S. Application Data

[62] Division of Ser. No. 439,310, May 11, 1995, Pat. No. 5,547,581, which is a division of Ser. No. 194,609, Feb. 10, 1994, Pat. No. 5,415,768, which is a continuation-in-part of Ser. No. 27,699, Mar. 8, 1993, Pat. No. 5,360,540, which is a division of Ser. No. 819,828, Jan. 13, 1992, Pat. No. 5,200,068, which is a continuation-in-part of Ser. No. 792,902, Nov. 15, 1991, Pat. No. 5,192,432, which is a continuation of Ser. No. 512,970, Apr. 23, 1990, abandoned.

[51] Int. Cl.⁶ .............................. H01G 4/35; B01D 15/08
[52] U.S. Cl. .................. 361/302; 210/198.2; 210/656; 204/600; 204/647; 204/671
[58] Field of Search .................. 361/302, 303–306.1, 361/307, 503, 504, 508, 511–512, 516, 517, 523, 528, 530, 532, 533, 535, 540; 333/182–183; 174/143, 152 R, 152 GM; 210/198.2, 635, 656; 204/600, 645, 647, 671

[56] References Cited

U.S. PATENT DOCUMENTS

| | | |
|---|---|---|
| 2,555,487 | 6/1951 | Haugaard . |
| 2,741,591 | 4/1956 | Dewey . |
| 2,853,448 | 9/1958 | Heiskell . |
| 3,324,026 | 6/1967 | Waterman . |
| 3,450,624 | 6/1969 | Natelson . |
| 3,451,918 | 6/1969 | Kolin . |
| 3,640,813 | 2/1972 | Nerenberg . |
| 3,658,674 | 4/1972 | Benak . |
| 3,846,274 | 11/1974 | Gifford . |
| 3,847,773 | 11/1974 | Snyder . |
| 4,049,534 | 9/1977 | Posner . |
| 4,057,482 | 11/1977 | Candor . |
| 4,560,445 | 12/1985 | Hoover et al. . |
| 4,743,373 | 5/1988 | Rai et al. . |
| 5,192,432 | 3/1993 | Andelman . |
| 5,196,115 | 3/1993 | Andelman . |
| 5,200,068 | 4/1993 | Andelman . |
| 5,360,540 | 11/1994 | Andelman . |
| 5,384,685 | 1/1995 | Tong et al. . |
| 5,415,768 | 5/1995 | Andelman . |
| 5,425,858 | 6/1995 | Farmer . |
| 5,538,611 | 7/1996 | Otowa . |

OTHER PUBLICATIONS

Johnson et al., The Electrosorb Process for Desalting Water, The Office of Saline Water Research and Development Progress Report No. 516, U.S. Dept. of the Interior PB 200 056 pp. i,ii,iii, and 1–30, Mar. 1970.

(List continued on next page.)

*Primary Examiner*—Bot L. Ledynh
*Attorney, Agent, or Firm*—Richard P. Crowley

[57] ABSTRACT

A flow-through capacitor and a controlled charge chromatography column system using the capacitor for the purification of a fluid-containing material, which column comprises an inlet for a fluid to be purified and an outlet for the discharge of the purified fluid, and a flow-through capacitor disposed within the column. The flow-through capacitor comprises a plurality of spirally-wound, stacked washer or rods to include a first electrically conductive backing layer, such as of graphite, and a first high surface area conductive layer secured to one side of the backing layer, such as carbon fibers, and a second high surface area conductive layer secured to the opposite side of the backing layer, the high surface area material layers arranged to face each other and separated by a nonconductive, ion-permeable spacer layer to insulate electrically the backing and conductive layer. The system includes a DC power source to charge the respective conductive layers with different polarities whereby a fluid-containing material passing through the column is purified by the electrically conductive, high surface area stationary phase and the retention thereof onto the high surface area layer and permitting, for example, the purification of aqueous solutions of liquids, such as salt, and providing for the recovery of a purified liquid.

50 Claims, 7 Drawing Sheets

OTHER PUBLICATIONS

Johnson et al., "Desalting by Means of Porous Carbon Electrodes," J. Elecrochem. Soc.: Electrochemical Technology, pp. 510–517, Mar. 1971.

Ganzi, "Water Purification and Recycling Using the CDI Process Environmental Progress," vol. 11, No. 1, pp. 49–53, Mar. 1971.

Bassler & Hartwick, "Electrically Conductive Stationary Phases for HPLC," AICHE Meeting in San Francisco, CA, Abstract, Nov. 1989.

Antrim et al., "Electrochromatography—A Preliminary Study of the Effect of Applied Potential on a Carbonaceous Chromatographic Column," Anal. Chim. Acta., p. 283, 1984.

Baledel et al., "Continuous Quantitative Electrolysis," Anal. Chem, pp. 1245–1251, vol. 36, No. 7, Jun. 1964.

Strohl et al. "A Packed Graphite Cell for Thin–Layer Chromatography," Analytical Letters 2(8), pp. 423–431, 1969.

Fujinaga, T., "Electrolytic Chromatography and Coulometric Detection with the Column Electrode," Pure Applied Chemistry, pp. 709–726, 1971.

Herne et al., "Modified Graphites for Chelation and Ion Exchange," Analytical Chemistry, vol. 50, No. 14, pp. 1954–1959, Dec. 1978.

Stoner et al., "Absorption of Blood Proteins on Metals Using Capacitance Techniques," Journal of Physical Chemistry, vol. 74, No. 5, pp. 1088–1094, Mar. 1970.

"KF for Electro Double Layer Capacitors," Toyobo Co. Bulletin, PCF 110, Sep. 1984.

Waldrop, Science, vol. 247, p. 161, Jan. 1990.

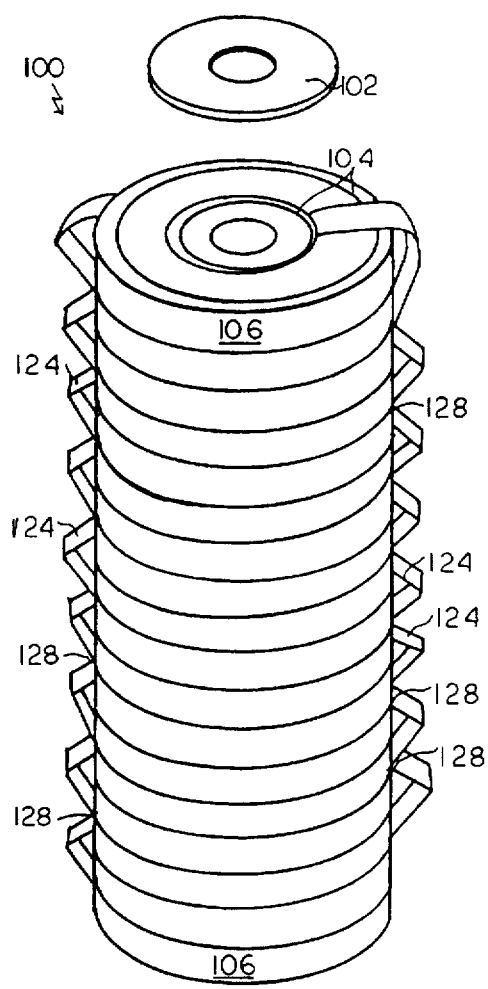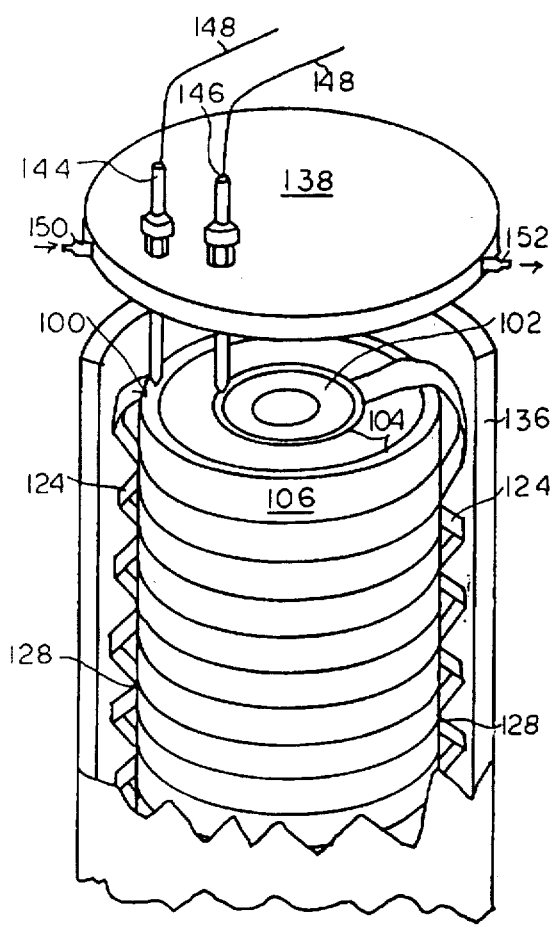
FIG. 6
FIG. 7

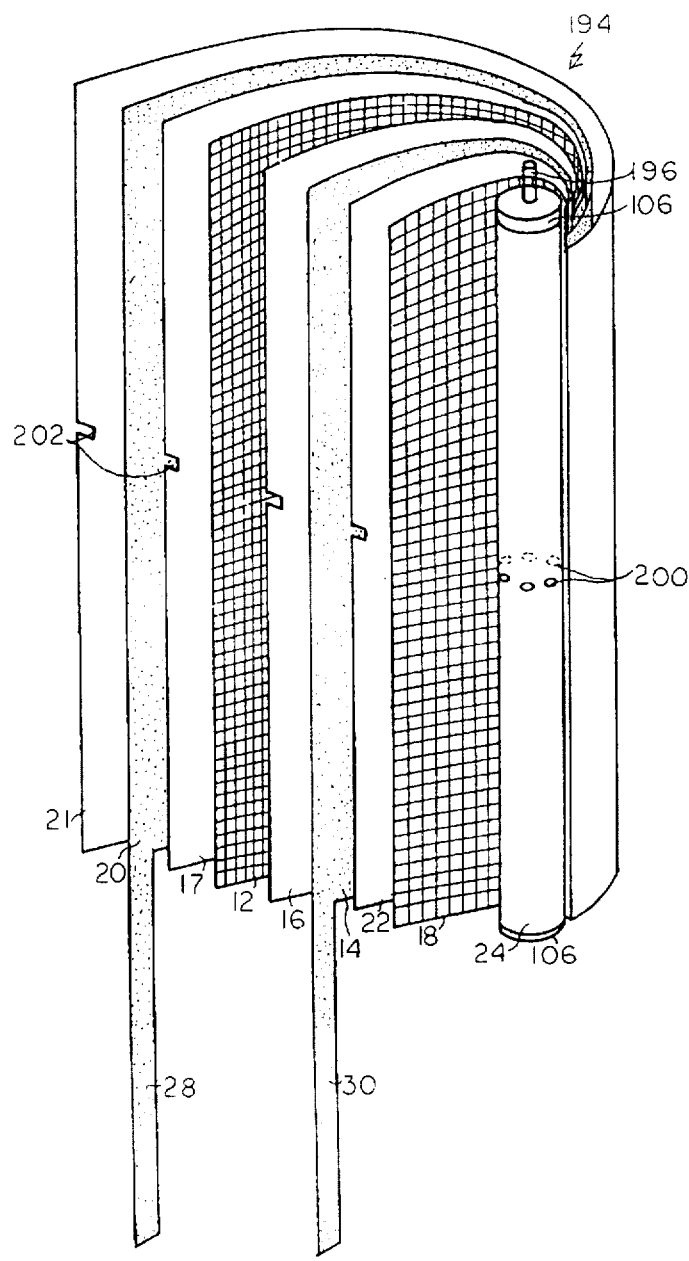
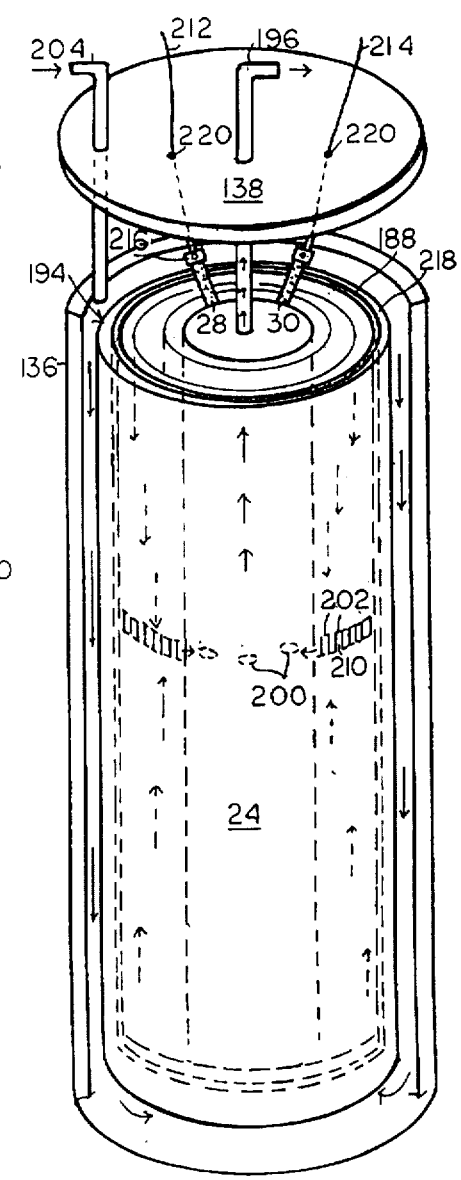
FIG.13
FIG.14

FLUID SEPARATION SYSTEM WITH FLOW-THROUGH CAPACITOR

REFERENCE TO PRIOR APPLICATIONS

This application is a divisional of U.S. Ser. No. 08/439,310 filed May 11, 1995, now U.S. Pat. No. 5,547,581, which is a divisional of U.S. Ser. No. 08/194,609 filed Feb. 10, 1994, now U.S. Pat. No. 5,415,768 issued May 16, 1995, which is a continuation-in-part of U.S. patent application Ser. No. 08/027,699, filed Mar. 8, 1993, now U.S. Pat. No. 5,360,540 issued Nov. 1, 1994 which is a divisional of U.S. patent application Ser. No. 07/819,828, filed Jan. 13, 1992, now U.S. Pat. No. 5,200,068, issued Apr. 6, 1993, which is a continuation-in-part application of U.S. patent application Ser. No. 07/792,902, filed Nov. 15, 1991, now U.S. Pat. No. 5,192,432, issued Mar. 9, 1993, which is a continuation of U.S. patent application Ser. No. 07/512,970, filed Apr. 23, 1990, now abandoned. U.S. patent application Ser. No. 07/760,752, a divisional application of U.S. patent application Ser. No. 07/512,970, was filed on Sep. 16, 1991 and is now U.S. Pat. No. 5,196,115, issued Mar. 23, 1993. All of these patents and the application are hereby incorporated by reference.

BACKGROUND OF THE INVENTION

The prior patents are directed to a flow-through capacitor and the use of the flow-through capacitor in a controlled charge chromatographic column and system and to a method of operation of the flow-through capacitor and chromatographic system, all directed to the purification of liquids. In one embodiment, the flow-through capacitor comprises a spirally-wound flow-through capacitor comprising a plurality of adjacent layers, and typically, wound about a porous, nonconductive tube and containing anode and cathode leads adapted to be connected to a DC power supply to provide for activation of the anode and cathode. In another embodiment, the invention is directed to a flow-through capacitor in a stacked column form about a central porous nonconductive tube and also for use in a chromatographic column and system for the purification of liquids. Both the spirally-wound and the stacked column flow-through capacitors are adapted to be placed within a housing with an inlet for the introduction of a liquid to be purified and an outlet for the discharge of a purified liquid and a concentrated liquid.

The flow-through capacitor comprises: a plurality of adjacent, alternative layers of a spacer layer comprising a non-electrically conductive, ion-porous spacer, such as nylon cloth, to permit the flow of liquid therethrough; an electrically conductive backing layer, such as graphite foil, and a high surface area layer on the conductive backing layer comprising a high surface area, electrically conductive layer, such as activated carbon, to act as the stationary phase, for example, of a chromatographic column. As disclosed, a plurality of the layers are first and second spacer layers, backing layers and surface area layers arranged in a spiral or a stacked column form housing and then anode and cathode leads connected, e.g. integrally and respectively, to the first and second backing layers, and to a DC power source to provide separate and opposite electrical charges on the backing layers and on the high surface area layers. The fluid is passed through the flow-through capacitor, such as, for example, an aqueous salt solution, to provide for the recovery of a concentrated salt and a purified liquid.

It is desirable to provide for a new and improved flow-through capacitor, chromatographic system and method to simplify the construction and manufacture of the flow-through capacitor, system and method and which provides for an increased efficiency in the purification of fluids.

SUMMARY OF THE INVENTION

The present invention relates to a flow-through capacitor and method of manufacture and operation and a chromatographic system and method employing the flow-through capacitor for the purification of fluids.

The invention concerns a flow-through capacitor for use in the electrical separation of a fluid, such as for example, but not limited to, a liquid containing one or more ionic components therein to be separated or concentrated, and which flow-through capacitor comprises a porous, first high surface area, electrically conductive material to act as an anode and a porous, second high surface area, electrically conductive material to act as a cathode. The capacitor also includes an ionically conductive or permeable, electrically insulating spacer material between the first and second high surface area materials to isolate electrically the first and second, high surface area materials. The first and second high surface area materials are configured in the flow-through capacitor to face directly each other with only the spacer material intervening. The flow-through capacitor also includes electrical leads adapted to connect the anode and cathode of the respective high surface area materials to a source of electrical power, and typically includes a housing to contain the flow-through capacitor with an inlet to direct a fluid to be separated into the flow-through capacitor and into the space between the first and second high surface area materials of the capacitor, and an outlet to recover the separated, purified fluid stream and a concentrated fluid stream.

It has been discovered that a significant and surprising improvement in the efficiency of the electrical separation or purification of a fluid is accomplished when the geometry of the flow-through capacitor is designed such that the first and second high surface area layers directly face each other across only an insulating spacer layer without the employment of a conductive backing layer interposed therebetween. Optionally, where a conductive backing layer is employed, the flow-through capacitor includes electrically conductive backing material layers having opposite sides and with the first and second electrically conductive high surface area materials disposed respectively and secured to the opposite sides of a pair of the conductive backing material to produce a flow-through capacitor which includes adjacent layers, either in spiral, stacked, rod or tube form or in other geometry form, comprising a first high surface area material and electrically conductive backing material and a second high surface area material and an electrically nonconductive spacer material adjacent either side of the first high surface area material and the second high surface area material to form an anode-cathode unit of the flow-through capacitor.

A wide variety of different geometries may be employed in the flow-through capacitor consistent with having the high surface area material representing the anode and cathode pairs of each anode-cathode unit facing each other as alternating anode-cathode pairs to enhance the quality and efficiency of the electrical fluid separation. The anode and cathode units may be partially or completely enclosed employing electrically conductive backing layers with the high surface area material generally in layer form facing each other or by omitting the electrically conductive backing layer material entirely and using the first and second high surface area material, an anode-cathode of enhanced or intrinsically greater electrical conductivity. Since the proportion of the high surface area material or layer is increased in the present geometry relative to the optional use of electrically conductive backing layers and insulating spacer materials and layers, the amount of either required is also reduced, which permits a more compact geometry and allows the anode and cathode layers to be closer to each other; therefore, diminishing harmful, internal resistance of the flow-through capacitor. It has been discovered that a flow-through capacitor of this type of geometry provides for increased speed of purification of the fluids therethrough and with an increase in the efficiency of the fluid purification.

The invention also includes a method for the purification of a fluid containing one or more ionic components therein by electrical separation and which method comprises introducing a fluid, particularly a liquid having one or more ionic components therein to be removed or reduced in concentration, into the inlet of a housing which contains a flow-through capacitor as described, with the anode and cathode of each anode-cathode unit in the flow-through capacitor electrically connected to a DC power supply to provide a controlled charge on the anode-cathode layers in the flow-through capacitor. The method includes passing the liquid to be purified between the direct facing anode-cathode layers and within the spacer material, while the anode and cathode have different charges to permit controlled charge absorption of one or more of the ionic materials in the fluid to be purified onto the one or both high surface area materials; and discharging the purified fluid from the outlet of the housing and removing periodically a concentrated liquid containing the absorbed ionic materials. The method is particularly adapted to the employment of an aqueous solution containing one or more ionic salts to provide a purified aqueous solution with removal or reduction or separation of one or more of the ionic salts in the solution.

The high surface area conductive material employed in the flow-through capacitor may be employed in various forms, but usually is employed in layer-type form. The high surface area material useful in the practice of the invention may comprise a wide variety of electrically conductive materials, alone or in combination, such as, but not limited to: activated carbon in particle, fiber, or mixtures thereof; activated carbon particles bonded or retained together with a binder material to form a continuous high surface area material; woven or non-woven activated carbon fibrous sheets or cloth; compressed, activated carbon particles or fibers; or metal, electrically conductive particles. The high surface area material may include one or more electrical conductivity enhancing additives or treatments, such as the use of activated carbon fibers or particles coated or plated with a conductive material of metal like palladium or platinum series black. For example, one high surface area material comprises compressed, activated carbon particles or fibers or mixtures with homogeneous mixed conductivity enhancers, such as graphite, acetylene black, noble metals or noble metal plated materials, fullerenes, or conductive ceramics or conductive polymers. In another example, the high surface area material may comprise a woven carbon fiber cloth with activated carbon strands interwoven or admixed with strands of a material of enhanced electrical conductivity, including graphite fibers, noble metals and conductive polymers. The high surface area material may include conductive ceramics, conductive polymers, fullerene material, azite and other conductive material. The electrical conductivity of the high surface area material may be enhanced by employing an electrically conductive backing material as a backing layer, or by adding electrical conductivity enhancers, such as powdered graphite and acetylene black homogeneously mixed therewith, or by using a high surface area material which itself is intrinsically, highly electrically conductive without any backing layer or enhancer. The high surface area material may also be activated carbon treated with a chemical, like alkali, such as potassium hydroxide, or a halogen, like fluorine; to increase the surface area and conductivity. Activated carbon material of greater than about 1000 square meters per gram surface area are preferred.

In one embodiment, the high surface area comprises an activated carbon fiber woven layer which provides for electrical conductivity and high porosity, although any other material which is highly electrically conductive and which has micropores can be employed for the high surface active area.

Optionally but desiredly, where the separation of certain fluids are involved, such as with biological fluids, proteins and organic molecules, the high surface area material may be processed or treated to reduce the adhesion or absorption of such molecules to the high surface materials. Typical treatments would include the use of fluorocarbons, silicones, and other surfactant-type materials on the high surface area materials.

Another material which may be employed as the high surface area layer comprises a material known as azite, a black, ceramic-like substance, which is highly porous and very strong and yet electrically conductive and is composed of a synthetic carbon polymer whose structure is flat with holes or pores. In addition, it is desirable to provide for chemical modification of the high surface area electrically conductive layer by the employment of adsorbing molecules thereon to alter the electrical characteristics, such as for example, adsorbing an aromatic molecule that contains a charge group onto the carbon cloth material layer which chemical modification of the surface active area may act as an ion exchanger. Azite material consists of micropores which provide superior capacitance properties due to the elimination of one diffusion barrier, that is, macroporous and microporous layers, and is easy to fabricate. Azite material provides for a three dimensional structure and may thus be used alone in connection with merely a non-porous dielectric spacer to provide a flow-through capacitor. In addition, since the three dimensional structure of azite is flat with holes, convective flow right through the pores of the material allows a faster method of purification than other materials, such as activated carbon and platinum black, where the porosity is on the surface, and slower processes of electrodiffusion set a limit on the speed of separation.

The insulating spacer material, usually in layer form, is placed between the high surface area material to provide electrical insulation of the anode-cathode pair and is fluid porous and nonconductive to the flow of electrons, but which is ionically permeable or conductive to allow the passage therethrough of ions or ionic carriers. The insulating material may comprise a porous woven or non-woven fibrous material composed for example of polymeric or natural fibers or mixtures thereof, such as olefinic fibers, like polypropylene; polyamide fibers, like nylon; fiberglass; polyester fibers and fluorocarbon fibers. The insulating material may also comprise microporous, polymeric membrane materials of ionically conductive materials, such as fluorocarbon, polyamide membranes, like Nafion® material (a trademark of E.I. Du Pont de Nemours & Co.). The insulating material may also comprise nonconductive particles, such as ceramic, silica, polymeric or other non-insulating material particles, alone or in a mixture formed in a bed on sheet material. The insulating spacer material generally has a thickness of less than about 10 mils and a porosity or molecular cut off of less than about 30 microns, e.g. 10 microns or less, and requires a cut-off of less than the molecular cut-off of the conductive high surface area material.

The flow-through capacitor is composed of at least one and typically a plurality of the alternating anode-cathode units, or, if desired, may be prepared and formed in various geometric forms and may include a spiral-wound, washer or disk stacked or flat sheet comprising one layer of a high surface area material, each with or without an electrically conductive backing layer and omitting the second insulating layer. The anode-cathode pairs may also comprise rod or tube-like geometries. The composite tubes or rods may be any geometrical shape, including polygons, like hexagons, square, rectangles, triangles or be circular or elliptical. Moreover, each single high surface area layer may have one or multiple conductive solid rods or tubes running inside or through the material to provide greater conductivity.

Electrical leads are connected to each of the alternate anode-cathode pairs of electrodes, either connected directly to the high surface area material where no conductive backing layer is used or to the electrically conductive backing material.

In one preferred embodiment, the electrical leads are integrally formed and extend from the high surface area material or the conductive backing material, which integrally formed leads reduce electrical resistivity. The electrical leads connect the series of separate anode-cathode units and are connected to a DC power supply.

The conductive backing material, such as in layer or other form, where employed, can be composed of any electrically conductive material, such as a metal film, for example, of aluminum, or more particularly, of an electrically conductive carbon, particularly graphite, in thin foil form. Where used, the high surface area electrically conductive material is secured or placed adjacent and on both sides of the electrically conductive backing material. Generally, the conductive backing material comprises a graphite foil or a conductive metal like silver or titanium or other metal or alloys, on which palladium or platinum black is electrodeposited to enhance the conductivity, and also selected for their corrosion-resistant properties. Optionally and preferably, the conductive backing material may be porous and, for example, have a plurality of holes to permit liquid flow therethrough.

The thickness of the high surface area material and the spacer material and the conductive backing material, where employed, may vary as desired, and generally may range, for example, from about 1.0 to 10 mils for the conductive backing material, where employed, and from about 25 to 300 mils for the high surface area material and about 10 to 100 mils for the spacer material.

The flow-through capacitor may comprise a spirally-wound flow-through capacitor which comprises a plurality of spaced apart layers of the selected material with the high surface area material layers facing each other and separated by the insulating spacer material and optionally on either side of a conductive backing layer, the spacer material defining a flow channel to permit the flow of the fluid therethrough and the layers spirally-wound about a hollow central core, the central core acting as the inlet or outlet of the flow-through capacitor and typically being porous or having a plurality of holes throughout its length so as to permit the fluid to be separated or purified into the porous spacer layer. The flow path of the fluid may be down through the central core from the outside of the flow-through capacitor. Generally, the flow-through capacitor may be sealed at each end and has anode and cathode leads typically which are integral with the high surface area material layer or with the conductive backing layer where employed, which leads are adapted to be connected through insulation in the housing to a DC control power supply and control system.

In another embodiment, the flow-through capacitor may comprise a plurality of stacked washers or disks secured about a central, nonconductive porous tube or support means with the washer ends sealed. The central tube may be porous or have holes punched therein or may be a rod having a plurality of longitudinal grooves therein for the passage of fluid. The washers or disks may comprise in series a first high surface area layer separated by an insulating layer and facing a second high surface area layer or where, optionally, a conductive backing is employed, high surface area layers are secured on the opposite sides of the backing, and thus comprise a sequence of each anode-cathode unit of an electrically conductive backing layer, a high surface area layer on one side of the backing layer and an insulating spacer material layer, and on the opposite side of the backing layer, a second high surface area layer and an insulating layer. Generally, the washers are arranged in sequence as described and stacked about the central tube and secured together in a compressed, contacting arrangement for the pressure of threaded end caps or threaded rods on each side or other means within a housing. The number of stacked washers may vary as desired. The flow-through capacitor may be placed within a cartridge or a housing, such as a standard filter cartridge, with the cartridge or housing having a combination anode and cathode rod, for example, of graphite, extending therethrough and connected to the electrically conductive high surface area layers alone or through the conductive backing material. The housing or cartridge includes an inlet for the introduction of the fluid to be separated. Generally, the purified liquid is then withdrawn from the tube at the outlet.

Where employed, the electrically conductive backing material may be employed in film, fiber, rod, tube or foil-type form and have the high surface area material secured or bonded and placed adjacent in any manner on the opposite surface thereon, so that the high surface material will face each other with an intervening, insulating material in between.

The controlled charge chromatography or other system employing the flow-through cartridge may be employed for the separating of a wide variety of fluids and more particularly, any solute, solvent or liquid system that wants to be concentrated or purified by resolving into separate species. The solvent can be polar, such as water, or non-polar, such as an aromatic, which fluid contains material which has selectivity for the solid phase and which can be modulated by controlling the charge of the solid phase, that is, the high surface area layer. For example, the solution may be of deionized water with resolved bands of ionic species, such as sodium chloride or other salts, and also any other types of molecules, organic, inorganic or biological. The invention will be disclosed for the purposes of illustration in connection with the separation of ionic liquid solutes; however, the system and method may be advantageously employed and used in the separation of other fluids, such as, but not limited to: non-ionic solutes, like hydrophobic solutes, or other fluids which contain one or more components which interact or are affected by electrically conductive surfaces, for example, liquids containing DNA, viruses, bacteria, cells, colloids or mixtures thereof. The flow-through capacitor permits the control of the charge on the stationary phase as the high surface area phase of the flow-through capacitor.

Typically, the spiral-wound flow-through capacitor having a central tube employs glue or a resin sealer at the ends for assembly and insertion into a cartridge housing. In operation, the fluid is introduced into the central tube and flows radially outwardly or, more frequently, is introduced between the exterior of the spiral-wound flow-through capacitor and the interior of the housing and flows radially inwardly toward the central tube.

In another embodiment of a spiral-wound flow-through capacitor, a flow-through capacitor is assembled without the need for end glue and sealing adhesives by the use of a shrinkable, tight or snug-fitting polymeric tube or shroud about the exterior of the flow-through capacitor, such as, for example, the use of a heat-shrinkable polymer wrapped about the exterior surface of the spiral-wound flow-through capacitor. Any shrinkable sheet material can be used generally in tube form which is placed about the capacitor and then shrunk by the application of heat, radiation or other means. For example, heat-shrinkable fluorocarbon polymers, like Teflon®, or olefinic polymers, like polyethylene, can be used. In this embodiment, the central tube or conduit in the spiral-wound capacitor has one or more holes in a selected position in the tube, generally at the middle of the tube, and usually spaced apart and uniformly arranged about the tube periphery. The central tube is sealed at both ends instead of sealing the capacitor layers themselves as in a typical spiral-wound arrangement. A gap is required in the surrounding high surface area material layer by cutting slots or holes therein and aligning the cut holes or slots with the holes in the central tube to form a radial flow path. In this embodiment, fluid flow passes both downwardly and upwardly alongside the layers of the spiral-wound capacitor until the fluid reaches the central gap or hole in the central tube and the fluid is withdrawn from the outlet at all or both ends of the central tube or conduit. This embodiment permits the easy assembly of the spiral-wound flow-through capacitor within a cartridge for use without the use of end-sealing resins and adhesives by the use of an outside liner material and gaps or slots in the high surface material layers aligned in a flow relationship with holes in the central conduit.

The invention will be described for the purposes of illustration only in connection with certain embodiments; however, it is recognized that those persons skilled in the art may make various modifications, changes, improvements and additions to the embodiments or illustrated embodiments, all without departing from the spirit and scope of the invention.

BRIEF DESCRIPTION OF THE DRAWINGS

FIG. 6 is a perspective view of the assembled flow-through capacitor of FIG. 5.

FIG. 7 is a fragmentary, partially sectional, schematic illustration of a controlled charge chromatographic column of the invention with the flow-through capacitor of FIGS. 5 and 6.

FIG. 13 is a schematic, partially exploded, perspective view of another embodiment of a spiral-wound flow-through capacitor of the invention.

FIG. 14 is a schematic, partially sectional view of a fluid separation system with the flow-through capacitor of FIG. 13 within a housing cartridge.

DESCRIPTION OF THE EMBODIMENTS

Figure 1:
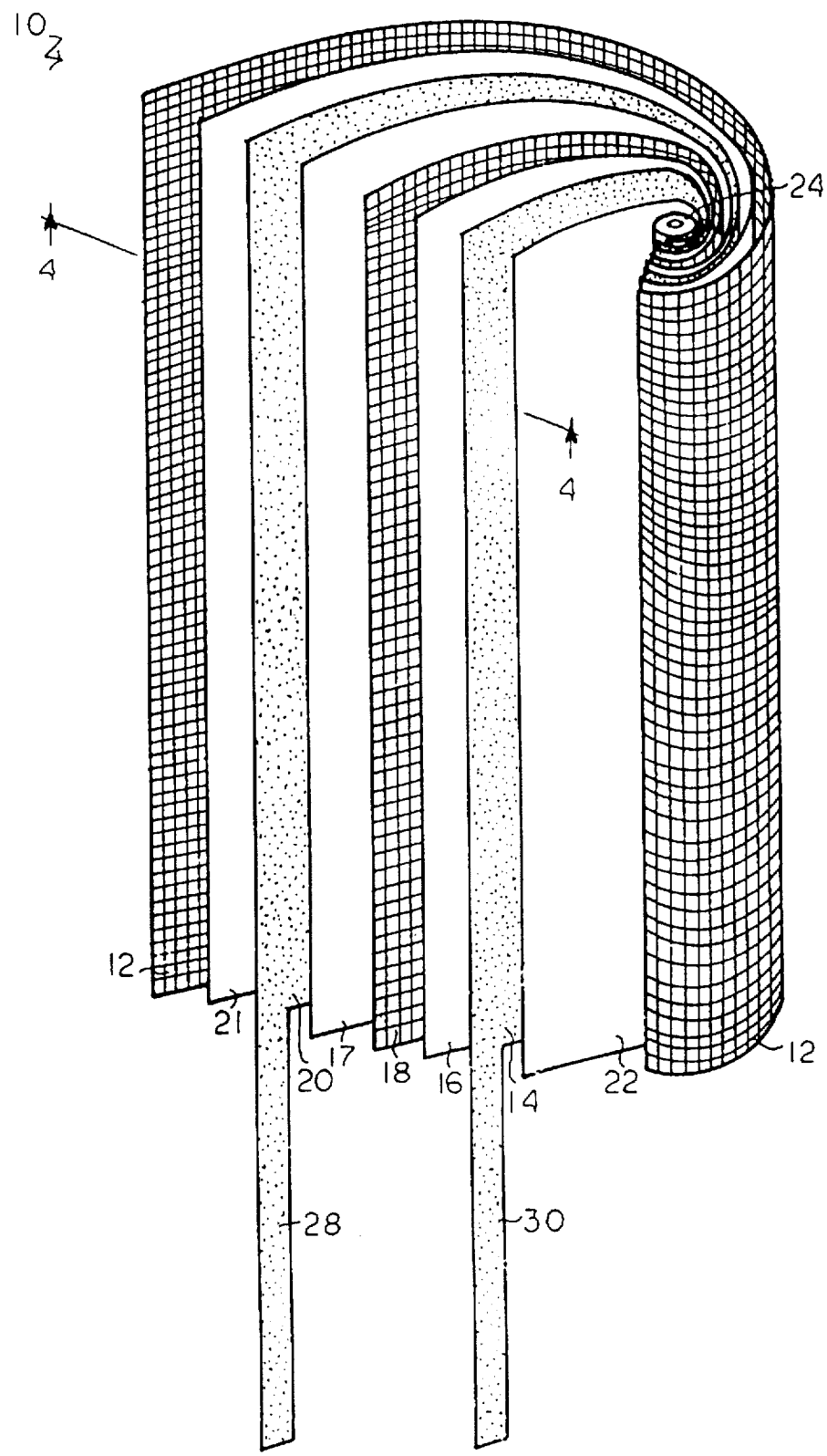
FIG. 1 is an illustrative, schematic, partially exploded view of a spiral-wound flow-through capacitor of the invention.
Figure 2:
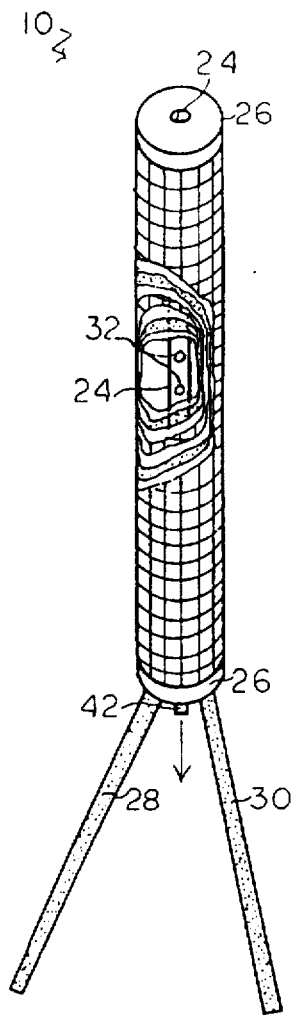
FIG. 2 is a schematic, illustrative, partially sectional view of the completed, spiral-wound, flow-through capacitor of FIG. 1.

With particular reference to FIGS. 1 and 2, there is shown a spiral-wound flow-through capacitor 10 comprised of a plurality of layers wound about a central plastic tube 24 having a plurality of perforations 32 therein extending down its length and having a one end which serves as an inlet for a fluid to be purified and an other end which serves as an outlet for the discharge of the purified fluid and the ionic species. Layers 12 and 18, which may be the same or different, form a nonconductive, insulating, porous, spacer sheet material having a thickness for example of about 5 mils to 50 mils, and more particularly, a layer of nylon woven cloth which forms a nonconductive spacer material between the anode and the cathode. Layers 14 and 20 comprise a conductive backing layer, which optionally may have holes punched therein to improve flow properties, and includes integral leads extending therefrom to act as electrical leads 28 and 30 for connection to a power source. For example, the conductive backing may comprise Union Carbide's Graphoilo® brand 5 mils thick graphite foil with pin holes punched therethrough. Layers 16, 17, 21 and 22 are comprised of a high surface area conductive material, and more particularly in the illustrated embodiment, an activated carbon woven fiber cloth to form a charge-holding, conductive high surface area (for example, cloth ANF #62 from Toyobo of Japan). The high surface area material layers 16 and 17 and 21 and 22 are bonded to opposite sides of the conductive backing layer 14 and 20, and directly face each other and are each separated only by the insulating material layers 12 and 18.

FIG. 2 is a schematic illustration of the flow-through capacitor of FIG. 1 wherein the layers have been wrapped around the central tube 24 wherein both ends are sealed with an epoxy resin 26 leaving open the inlet of the tube 24 and the outlet. FIG. 2 illustrates a partial sectional view that the inner tube 24 has a series of holes 32 therein, for example, 1 mm diameter holes, 1/10" apart, on a 3/16" outside diameter tube. In another embodiment, the capacitor may have no epoxy seals, and a solid tube, so that flow is between the layers. The capacitor may have the top end of the hollow tube sealed so that the direction of the flow is through the sides of the device, through the successive layers, and then out the open end of the inner hollow tube.

Figure 3:
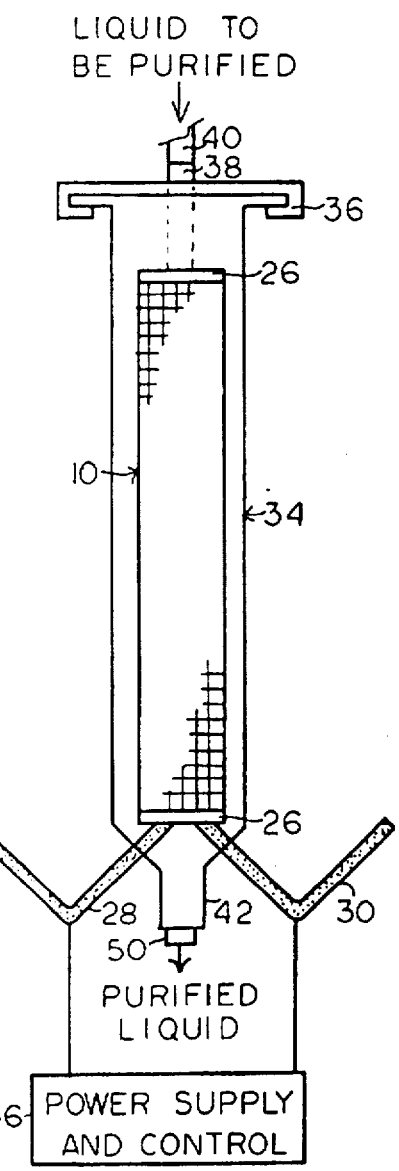
FIG. 3 is a schematic illustration of a chromatographic column and system employing the flow-through capacitor of the invention.

FIG. 3 is an illustration of chromatographic column 34 and system containing the flow-through capacitor 10 disposed therein and generally axially aligned with the axis of the column 34, the column having an end cap 36, an inlet 38 and connected to a tubing 40 for the introduction of a fluid material to be purified, the end cap gasketed to a defined pressure, for example, up to 100 psi, and the column 34 having an outlet 42. Extending from the column 34 are the conductive leads 28 and 30 which have epoxy seals where the outlet tubing 50 and the Graphoil® leads 28 and 30 come through column 34. For example, the column 34 may comprise a transparent, plastic, polypropylene, syringe-type barrel. Leads 28 and 30 are connected to an outside power supply and control 56.

Figure 4:
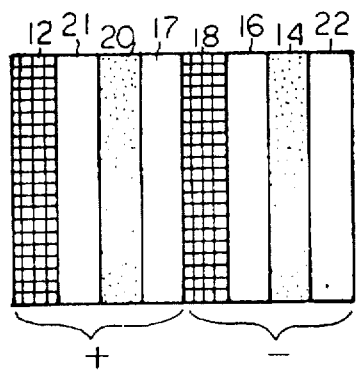
FIG. 4 is a sectional, enlarged view through line 4—4 of FIG. 1.

FIG. 4 is an enlarged sectional view of the flow-through capacitor of FIG. 1 illustrating that the respective high surface material layers 16, 17, 21 and 22 on opposite sides of separate, conductive backing material layers 14 and 20 and facing each other, but separated by the insulating layers 12 and 18, to provide an effective, improved flow-through capacitor with a pair of anode-cathode units.

The spiral-wound flow-through capacitor of FIGS. 1–4 was prepared employing as the high surface area material two 8"×3" pieces of 4 grams each of activated carbon cloth (American Kynol Co. of Pleasantville, N.Y. ACC-509-20) as the insulating spacer material, two 3"×5" pieces of nylon cloth 2 micron pore size (Tetko 3-5/2) and as the conductive backing layer, two 3"×4" pieces of a 5 mil graphite foil material (polycarbon). The activated carbon cloth was folded over the conductive graphite foil and the insulating material placed on either side and the layers then spiral-wound about a 3" long ¼ OD plastic tube with holes therein, the tube ends sealed, and the device placed in a pressure tight 30 cc syringe barrel as a cartridge, and a DC voltage of 2 volts applied to the conductive material leads. The device purified a 0.01M sodium chloride solution to better than 90% purity at a flow rate of 14 ml/minute at 2 volts. The recovered sodium chloride peak was greater than 0.05M concentration. A 0.1M sodium chloride solution was purified at 1 ml/minute to better than 80% purity. A flow capacitor using identical quantities of activated cloth but spiral-wound in alternating layers as in U.S. Pat. No. 5,192,432 with a flow rate of 14 ml/minute and 0.01M sodium chloride solution feed provided only 60% purification rather than 90% purification with the face-to-face, high surface area embodiment as shown.

Figure 5:
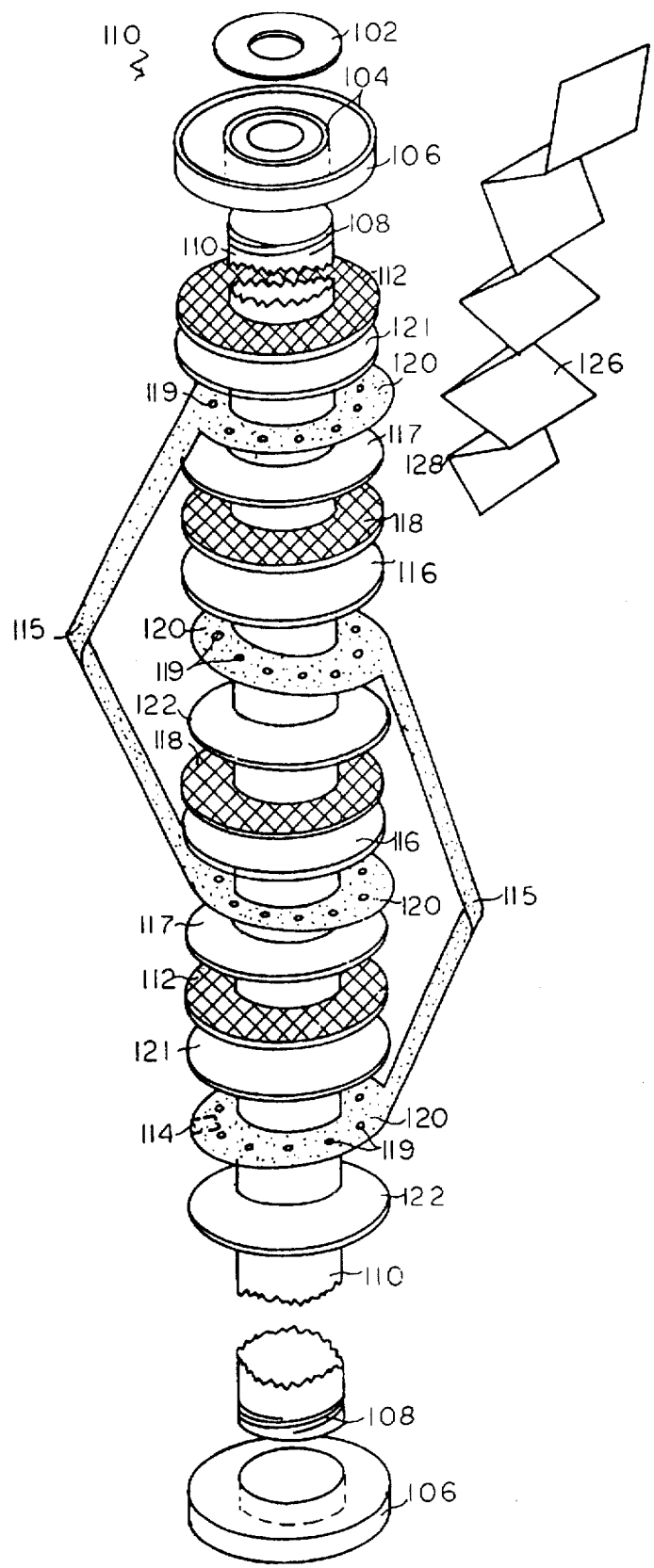
FIG. 5 is a schematic, illustrative, exploded view of a stacked washer flow-through capacitor of the invention.

FIG. 5 shows a stacked washer flow-through capacitor 100 in an exploded form having a rubber washer 102 at the top end thereof to form a watertight seal when the capacitor 100 is put inside a standard filter cartridge holder 136 (see FIG. 7). The cartridge 100 contains end caps 106 made of an inert, nonconductive material, such as for example, a high density polypropylene resin, with the end caps threaded on the inside to screw onto threads 108 on the end of a central tube 110. The top end cap includes two concentric circles of inert conductive material 104, such as for example, but not limited to: gold, gold foil, graphite or platinum series metals and the like. The central supporting tube 110 comprises a porous polyethylene tube, for example a 10-inch tube of porous plastic with a ⅜" outside diameter and a ⅛" wall thickness. The central tube 110 acts as a supporting member to hold the ring-shaped or washer parts together and under compression when the end caps 106 are threadably screwed against the ends of the central tube 110. The porous plastic tube 110 allows for flow out of the middle of the tube to the top end. The tube could also include a solid, rod-like element with longitudinal, fluted sides to provide support for the washer elements and also provide for flow out of the tube. Employment of a central, plastic, porous, polyethylene tube has the added advantage of being also a microfilter, for example, of one to five microns or less, so as to filter out any fine material which may leach off a carbon disk or other washer materials. The cartridge 100 includes a plurality of washer materials in sequence to include a porous, nonconductive spacer material with pores, for example, a synthetic, fibrous material or other type of nonconductive spacer material, such as fiberglass or woven nylon.

Washer material 120 comprises any inert, conductive backing material, for example, a 5-mil thick Graphoil® brand (Union Carbide graphite foil material) with multiple holes 119 perforated in it to provide for better liquid flow therethrough. This graphite foil material (also see FIG. 8) provides a pair of washer materials 120 connected with a connecting bridge 115 having an optional notch 114 to accommodate electrical communication to a conductive material. The tab or arm 115 connecting the two halves of the backing material 120 provides for the connecting tab or arm 115 to be crimped to form tabs that extend outside of the completed, assembled flow-through cartridge, which tabs can then be utilized for form conductive leads. In one preferred embodiment, the conductive leads having charge may be faced inwardly.

The washer material 116, 117, 121 and 122 comprises any high surface area conductive material. One example is the use of KX Industries extruded, activated carbon tubes which are held together with a small amount of polypropylene binder. These tubes are extruded in tube shapes 2" overall in diameter with an inner diameter which is widened to 1⅛" and cut into rings of about ⅛" thickness. Such high surface area conductive material 120 may also include activated carbon cloth full of activated carbon fibers, since the compression afforded by the stacked washer cartridge flow design would compress the loose material and allow it to become conductive by inner particle contact, thus allowing the choice of other inexpensive, conductive, high surface area conductive materials.

Figure 9:
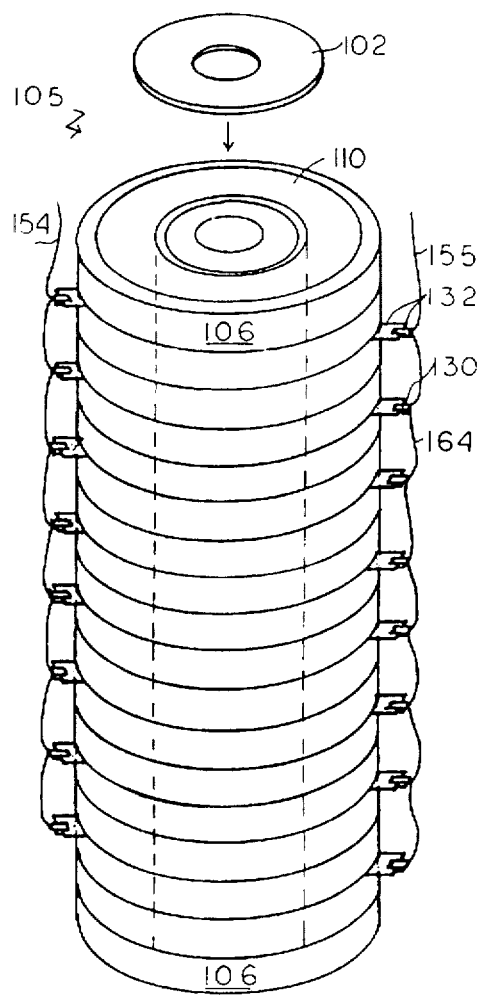
FIG. 9 is a perspective view of another embodiment of the assembled flow-through capacitor of FIG. 5.

The conductive leads material 126, as shown on the right hand side of the exploded diagram in FIG. 5, includes folded tab 128 which can be made of any electrically conductive material, such as for example, Graphoil®, or may also be a wire (as shown in FIG. 9) suitably coated to protect it from the environment or a naked inner wire of gold or platinum, along with the electrically conductive material, could be attached by a clamp 130 to the arm 118 or tab 132. The conductive material as illustrated in FIG. 5 is shown in corrugated form. The flat tab section 128 is designed to lie on top of parts 120 or 116, 117, 121 and 122 to form an electrical contact under compression. As illustrated, an optional notch 114 can be employed to accommodate thickness of the tab, while in many cases the other materials are compressible enough so this added notch need not be employed. The conductive leads 126 and tabs 128 short together the alternating layers composed of conducting layers 116, 117, 121 and 122 and 120 which are separated by the insulating spacer 112 and 118 to form alternating washer anodes and cathodes up and down the central tube 110.

FIG. 6 shows the assembled flow-through capacitor cartridge 100 showing the side leads 124 that short the alternating anode and cathode washer layers together in parallel. The tabs 128 are now pressed against the backing layers 120 to form electrical contact. The conductive leads 124 are also electrically connected on each of the conducting circles 104 in the end cap 106. The assembled flow-through capacitor cartridge 100 as illustrated in FIG. 6 is thus ready for insertion in a standard filter cartridge for use as a controlled charge chromatography system.

FIG. 7 is a fragmentary, partially sectional, schematic illustration of a controlled charge chromatography apparatus showing the use of the flow-through capacitor cartridge 100 within a standard filter cartridge 136 having a screw-on head 138 with the inlet 150 for the introduction of a liquid for a controlled charge chromatographic separation, and an outlet 152 for the removal of a purified liquid from the center of the central supporting tube 110. The cartridge head 138 is modified to allow watertight, electrically conductive leads 148 to an outside power supply with the employment of paired conductive rods, for example ⅛" graphite rods 144 and 146, having pointed ends, which are in electrical contact with the concentric circles 104 and the end caps 106 of the cartridge 100, with compression nuts used to form a watertight seal over the rods 144 and 146. Threaded inserts go in to the filter holder cartridge top 138 to corresponding threaded holes in the top cover for the employment of the rods 144 and 146 in a watertight fashion. The rods have leads 148 to a power supply (not shown, but see FIG. 3). The filter holder top 138 is screwed tightly to form a watertight seal against washer 102. The conductive rods 144 and 146 are pressed firmly against the concentric conducting circles 104, thereby forming electrical contact through to the leads 124. Since the washers are concentric, no matter how the top is screwed on, the rods 144 and 146 will always be positioned in the right place against conductive circles 104.

In operation, a liquid to be purified is introduced through inlet 150, 150 flows to the outside within cartridge 136, and goes through from the inside to the outside of the washer 102. Purified liquid is then removed through the central tube 110 and therefore through outlet 152. While the conductive backing material has been described in a particular form, that is, two washers 120 with a conducting arm bridge 115, this particular form is not essential to the operation of the flow-through capacitor of the invention, and obviously may be replaced by other forms, but the illustrated form represents one preferred embodiment employing the electrically conductive backing material in the stacked washer flow-through capacitor of the invention.

Figure 8A:
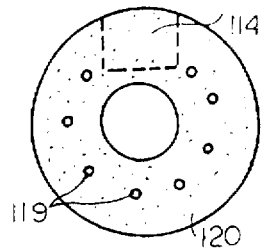
FIGS. 8A, B and C are top plan views of three embodiments of the conductive backing wash used in FIG. 5.
Figure 8B:
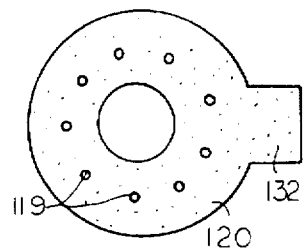
Figure 8C:
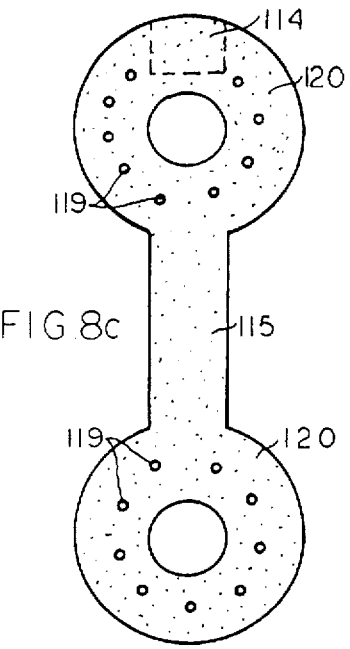

FIG. 8 shows three types of electrically conductive backing washers A, B and C. FIG. 8C shows a conductive backing washer 120 connected by connecting tab 115 with an optional notch 114, and multiple holes 119 perforated in it to provide for better liquid flow-through. FIGS. 8A and 8B show separate electrically conductive backing washers for layers, with FIG. 8A showing the optional notch 114 to accommodate electrical communication to a conductive material and FIG. 8B showing an extended tab 132 for attachment by clamp 130 of an electrically conductive wire or lead 134. Thus, as illustrated, a new, improved and unique flow-through capacitor and controlled charge purification chromatography column system and method have been discovered which provide for the effective and rapid separation by a flow-through capacitor of high electric capacitance and high surface area, high adsorption ability, electrically conductive, stationary phase in the chromatographic column.

FIG. 9 shows another embodiment of the flow-through capacitor 105 showing the tab arms 132 extending from the compressed washer assembly with electrically conductive clamps 130 connected to each other by an electrically conductive wire 164, which leads from the capacitor to a power supply by lead lines 154 and 155 on either side of the capacitor 105. The assembled flow-through capacitor cartridge 105 is thus ready for insertion in a standard filter cartridge for use as a controlled charge chromatography system.

Figure 10:
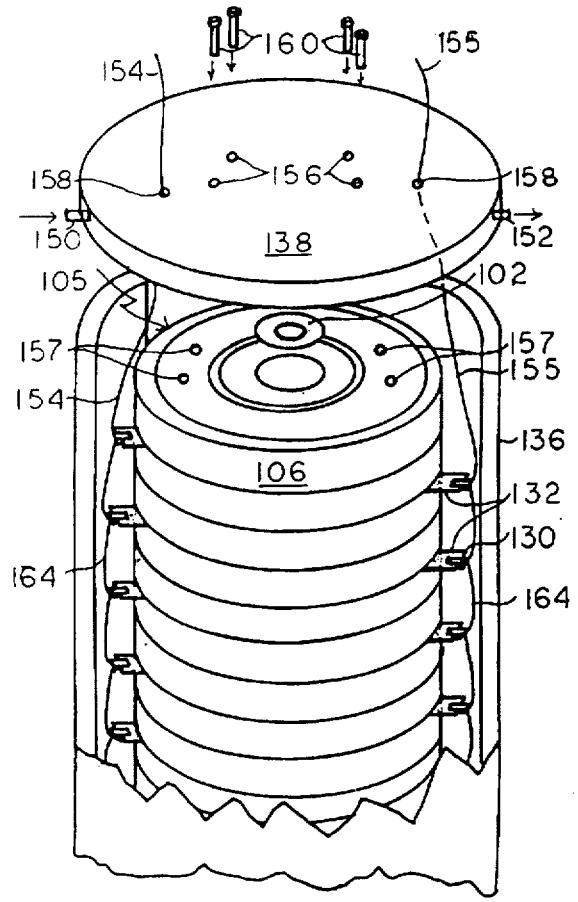
FIG. 10 is a fragmentary, partially sectional, schematic illustration of a controlled charge chromatographic column of the invention with the flow-through capacitor of FIG. 9.

FIG. 10 is a fragmentary, partially sectional, schematic illustration of a controlled charge chromatography apparatus showing the use of the flow-through capacitor cartridge 105 within a standard filter cartridge 136 having a screw-on head 138 with inlet 150 for the introduction of a liquid for a controlled charge chromatographic separation, and an outlet 152 for the removal of a purified liquid from the center of the supporting tube 110. The cartridge head 138 is modified to allow watertight, electrically conductive leads 154 and 155 to extend to an outside power supply (not shown) through holes 158. Threaded screws 160 screw into the filter holder cartridge top 138 through holes 156 to corresponding threaded holes 157 in the top cover 106 to seal the cover in a watertight fashion against washer 102.

Figure 11:
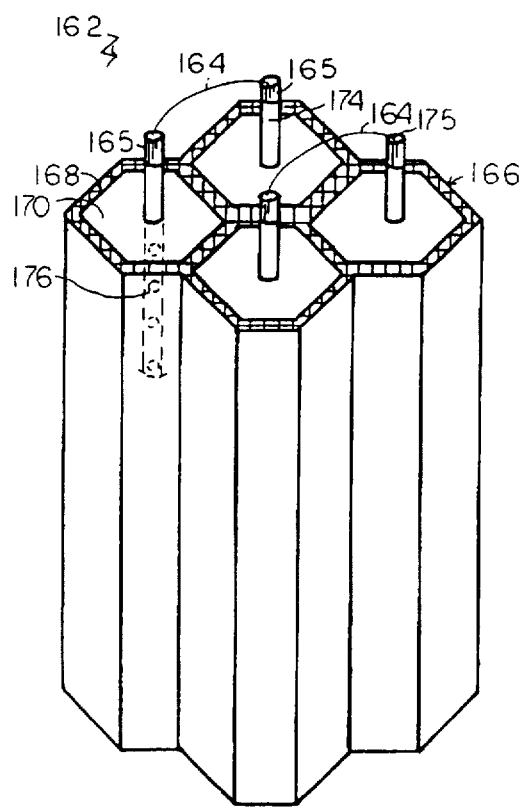
FIG. 11 is an enlarged, fragmentary, perspective view of a plurality of the flow-through capacitor rods.
Figure 12:
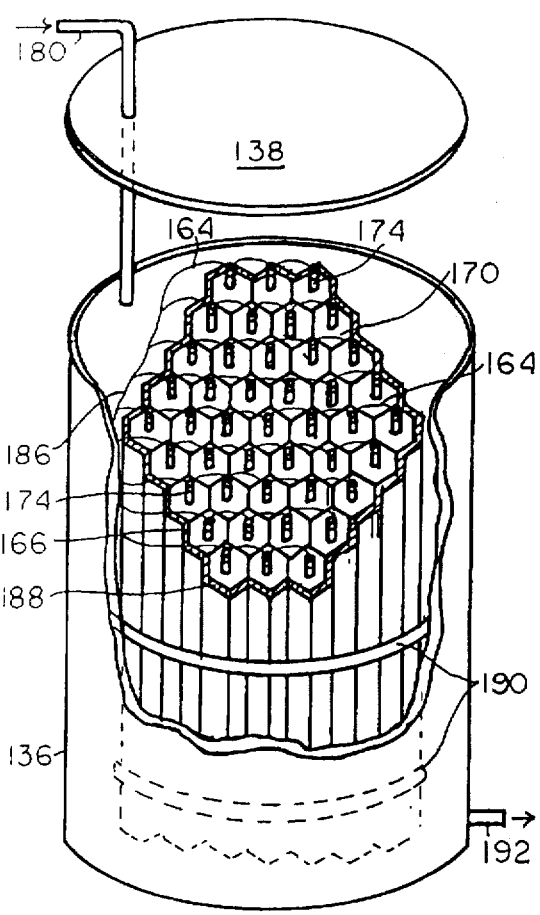
FIG. 12 is an enlarged, perspective, partially sectional view of a plurality of the flow-through capacitor rods of FIG. 11 within a housing cartridge.

FIGS. 11 and 12 illustrate an optional geometric form of the flow-through capacitor in a compact electrode bundle configuration 162. FIG. 11 illustrates the electrode bundles 166 consisting of high surface conductive material 170 with an optional conductive backing rod 174 with central hole 175 and side holes 176 to provide a fluid flow path into and radially through the high surface area material 170, surrounded and connected by ion permeable, non-electrically conductive spacer material 168 and individual lead lines 164 extending from the central holes 175 in the rods 174. The side holes 176 may be replaced, if desired, with a groove extending vertically along the rod 174. An electrical connector composed of a pair of cap-shaped metal clamps 165 at the end of electrical lead 164 is used to connect the ends of the graphite rods.

FIG. 12 is a perspective, partially sectional view of a plurality of electrode bundles 166 within a holder cartridge 136 with a screw-on top 138 having an inlet 180 for the fluid feed stream and an outlet 192 for the purified liquid. The individual electrode bundles 162, with conductive backing rods 174 extending therefrom are connected by electrically conductive lead lines 164 extending from the rods, which lead lines are then gathered into main lead lines 186, which pass out from the cartridge holder 136 to the power supply. The compact electrode bundle configuration 162 is held together by shrink wrapped teflon 188 applied to the outside of the bundles, and further by watertight gaskets 190 to seal the electrode bundle against the cartridge holder wall.

FIGS. 13 and 14 show a further embodiment of the spiral-wound flow-through capacitor assembly as shown in FIG. 1, comprised of a plurality of layers 12, 14, 16, 17, 18, 20, 21 and 22 wound about a central plastic tube 24 with end caps 106 to seal the ends of the tube, and an outlet fluid feed 196. The conduit 24 has a plurality of holes 200 evenly spaced around the circumference and at the mid-point of the central tube 24. Corresponding slots 202 are cut in the middle of the high surface area conductive material 16, 17, 21 and 22, which slots, when wound around the central tube 24, create a flow path for the liquid to be purified to pass through the filter layers. FIG. 14 shows the flow-through capacitor of FIG. 13 in a cartridge holder 136 with a screw-on lid 138 having two holes 220 in the lid to allow the main anode-cathode leads watertight egress to outside power supply, and a fluid inlet tube 204 and outlet 196. The spiral-wound capacitor assembly 194 is sealed by a shrink wrap with a teflon liner 188 and further wrapped by a plastic pipe 218. When wound in this manner, the slots 202 cut into the middle of high surface area conductive material layers 16, 17, 21 and 22 form gaps 210 which align with the holes 200 in the conduit tube 24 to allow the fluid to flow out through the center. Conductive leads 28 and 30) extend from the spiral-wound capacitor configuration to clamps 216 which attach the leads to the main anode lead 212 and main cathode lead 214 through holes 220 in the lid 138 to the power supply and control. With the spiral-wound flow-through capacitor shrink-wrapped in the teflon seal, the system does not require sealing caps or glue on the ends. In this manner the fluid is introduced through fluid inlet 204 and is passed both downward and upward alongside the layers until it reaches the central gap 210. It then travels through the holes 200 into the conduit tube 24, and then out through the outlet 196.

What is claimed is:

1. A fluid separator system for the electrical separation of a fluid containing separable components, which system comprises:
   a) a housing having an inlet for the introduction of a fluid to be separated and an outlet for the withdrawal of separated components or reduced component fluid;
   b) a flow-through electrical capacitor disposed in the housing, the capacitor comprising:
      i) a porous first high surface area electrically-conductive material layer to act as a stationary phase anode;
      ii) a porous second high surface area electrically-conductive material layer to act as a stationary phase cathode;
      iii) a spacer material layer between the anode and cathode to define a fluid flow channel to permit the fluid to contact the anode and cathode;
      iv) the first and second high surface area electrically-conductive material layers disposed to face each other externally on either side of the spacer material;
      v) a first electrically-conductive backing material layer;
      vi) a second electrically-conductive backing material layer;
      vii) the first and second electrically-conductive backing material layers disposed in electrical contact respectively with the first and second high surface area electrically-conductive material layers; and
      viii) electrical lead means from the anode and from the cathode; and
   c) a direct current power source connected to the electrical lead means to supply electrical power to the anode and cathode to provide for the adsorption-desorption of selected components of the fluid by the first or second high surface area material layers.

2. The system of claim 1 which includes control means to provide for the application of electrical charges to the cathode and anode for adsorption of components and for the shorting of the anode and cathode for the desorption of components.

3. The system of claim 1 wherein the electrical lead means are integrally formed and extend to the high surface area material or the electrically-conductive backing material.

4. The system of claim 1 which includes a source of fluid to be separated in fluid flow communication with the inlet of the housing.

5. The system of claim 4 wherein the fluid source comprises an ionic-containing liquid.

6. The system of claim 5 wherein the liquid comprises water with sodium chloride therein.

7. The system of claim 1 wherein the capacitor comprises a plurality of alternating anode and cathode pairs.

8. The system of claim 1 wherein the capacitor comprises a spirally wound module.

9. The system of claim 8 which includes an external polymeric shroud in a snug relationship about the exterior peripheral surface of the spiral wound module.

10. The system of claim 9 which includes:
    a) a plurality of aligned, radial, generally centrally, uniformly positioned slots in the spirally wound, high surface area material layers; and
    b) a central tube having holes therein aligned with the said slots in the high surface area material layers.

11. The system of claim 8 which includes a porous central tube and wherein the capacitor comprises a spirally wound module about the central tube.

12. The system of claim 1 wherein the capacitor comprises a plurality of bundled conductive rods to form a plurality of anode and cathode pairs.

13. The system of claim 1 wherein the capacitor comprises a plurality of stacked elements to form a plurality of anode and cathode pairs.

14. The system of claim 13 which includes a central porous tube and a plurality of stacked washer elements about the tube.

15. The system of claim 14 wherein the electrically-conductive backing material layers comprise alternating pairs of washer elements, each pair of backing washer elements integrally connected by an integral connecting, electrically-conductive tab to form the electrical lead means.

16. The system of claim 15 which includes a pair of corrugated, electrically-conductive tab elements alternately longitudinally placed on the external surface of the backing washer elements to form continuous connecting anode and cathode electrical lead means.

17. The system of claim 13 wherein the stacked elements comprise an extruded activated carbon material having a small amount of a polypropylene binder.

18. The system of claim 13 wherein the first and second backing materials are connected with tab elements.

19. The system of claim 1 wherein the capacitor includes a plurality of alternating anode and cathode pairs each of which pairs comprises:
    a) a porous, first electrically-conductive, high surface area material layer;
    b) a porous, second electrically-conductive, high surface area material layer;
    c) a first electrically-conductive backing material layer;
    d) the first and second high surface area material layers disposed externally on either side of the first backing material layer and in compressed electrical contact with substantially the total surface area of the backing material layer; and
    e) an ionically permeable, electrically insulating spacer material layer adjacent one surface of the first or second high surface area, electrically-conductive material layers.

20. The system of claim 1 wherein the spacer material layer is selected from the group consisting of: fibrous sheet material; microporous polymeric membrane sheet material; and particle-containing sheet material.

21. The system of claim 1 wherein the spacer material layer has a molecular cut off porosity of less than about 30 microns.

22. The system of claim 1 wherein the spacer material layer comprises a double layer whereby a fluid to be separated is introduced between the layers of the double layer spacer material.

23. The system of claim 1 wherein the spacer material layer comprises a woven polymeric sheet material having a thickness of about 10 to 100 mils.

24. The system of claim 1 wherein the spacer material comprises a porous spacer material to define the fluid flow channel.

25. The system of claim 1 wherein the spacer material comprises a non-porous spacer material.

26. The system of claim 1 wherein the first or second or both of the electrically-conductive material layers are carbon-containing three-dimensional structured layers.

27. The system of claim 26 wherein the three-dimensional structural layers comprise azite.

28. The system of claim 1 wherein the high surface area material layer has a surface area of greater than about 1000 square meters per gram.

29. The system of claim 1 wherein the high surface area material layers are selected from the group consisting of: activated carbon; conductive polymers; conductive ceramics; platinum series black; azite, fibrous carbon and combinations thereof.

30. The system of claim 1 wherein the first and second electrically-conductive material backing layers have holes therein for the passage of fluid.

31. The system of claim 1 wherein the electrically-conductive material backing layers comprise graphite or metal foil sheet materials.

32. The system of claim 1 wherein the high surface area material layer comprises activated carbon or treated activated carbon.

33. The system of claim 1 wherein the high surface area material layer comprises an activated carbon woven cloth, the backing material layers comprise a graphite sheet material and the spacer material layer comprises a polymeric layer.

34. The system of claim 1 wherein the capacitor comprises:
a) a plurality of generally parallel, longitudinal, high surface area rod elements forming a high surface area, electrically-conductive material layer;
b) a plurality of electrically-conductive backing rod elements extending longitudinally through each high surface area rod element to form a backing material layer;
c) insulating spacer material surrounding the exterior surface of each high surface area rod element; and
d) electrical lead means at the ends of each of the backing rod elements to form a plurality of separate cathode and anode pairs.

35. The system of claim 34 wherein the high surface area rod elements are polygonal-shaped elements and arrayed in a close, generally parallel, bundled arrangement.

36. The system of claim 35 wherein the high surface area rod elements are composed of activated carbon, and the backing rod elements are composed of graphite.

37. The system of claim 36 wherein the backing rod element comprises a tube having an inlet and an outlet and a plurality of holes along the length of the tube.

38. A fluid separator system for the electrical separation of a fluid containing separable components, which system comprises:
a) a housing having an inlet for the introduction of a fluid to be separated and an outlet for the withdrawal of the separated components or reduced component fluid;
b) a spiral wound, flow-through capacitor cartridge within the housing, which spiral wound capacitor comprises:
i) a central, electrically-insulating, porous tube having an inlet and an outlet for the passage of a liquid;
ii) a plurality of separate layers spirally wound about the central tube to form a spirally wound capacitor and which layers comprise:

a) an anode first and second porous, high surface area, electrically-conductive material layers as stationary phases, each having a surface area of greater than about 1000 $m^2/g$, and each composed of an activated carbon material;
b) a first electrically-conductive, porous backing material layer composed of a metal foil or graphite foil material, and having an integral electrical lead therefrom, and disposed in electrical contact with and between the first and second high surface area material layers to form an anode;
c) a first electrically-nonconductive, spacer material to define a fluid-flow channel between the anode and cathode;
d) a cathode first and second porous, high surface area, electrically-conductive material layers as stationary phases, each having a surface area of greater than about 1000 $m^2/g$ and each composed of an activated carbon material;
e) a second electrically-conductive, porous backing material later composed of a metal foil or graphite foil material, and having an integral electrical lead therefrom, and disposed in electrical contact with and between the first and second high surface area material layers to form an anode;
f) a second electrically-nonconductive, porous spacer material; and
g) the first spacer material separating layer facing adjacent the spiral wound, high surface area layers; and
iii) means to retain the spiral wound layers about the central tubes
c) a direct current power source connected to the electrical lead means to supply electrical power to the anode and cathode to provide for the adsorption-desorption of selected components of the fluid by the first or second high surface area material layers.

39. The system of claim 38 wherein the means to retain includes end caps at each end of the spiral wound layers and about the inlet and outlet of the central tube.

40. The system of claim 38 wherein the means to retain includes a polymer tubular material about the exterior peripheral spirally wound cartridge.

41. The system of claim 40 which includes a generally centrally positioned plurality of aligned slots in the high surface area spiral wound layers, and a plurality of generally centrally positioned, peripheral holes in the central tube generally aligned with the said slots.

42. A fluid separator system for the electrical separation of a fluid containing separable components, which system comprises:
a) a housing having an inlet for the introduction of a fluid to be separated and an outlet for the withdrawal of the separated components or reduced component fluid;
b) a flow-through capacitor cartridge within the housing which capacitor comprises:
i) a plurality of bundled together, generally parallel, longitudinal rod elements having a one and the other end, each rod element comprising:
a) a porous, high surface area, electrically-conductive material to form a high surface area rod element of selected exterior shape with an exterior surface; and
b) a central, electrically-conductive backing rod having a one and other end and within the high surface area rod element and composed of electrically conductive backing material;

ii) electrically insulating spacer material extending about the exterior surface and insulating each high surface area rod element and to define a fluid-flow channel between the anode and cathode;

iii) the high surface exterior face layer of each rod element facing another exterior face surface of an adjacent high surface area rod element and separated only by the spacer material;

iv) means to connect electrically the one or other end of each central backing rod to a source of electrical power to form a plurality of adjacent, alternating anodes and cathodes of the rod elements; and v) means to retain the rod elements in an arrayed, bundled form; and c) a direct current power source connected to the electrical lead means to supply electrical power to the anode and cathode to provide for the adsorption-desorption of selected components of the fluid by the first or second high surface area material layers.

43. The system of claim 42 wherein the central rod comprises a tube having a one and other end for the passage of a liquid therethrough.

44. The system of claim 42 wherein the central tubes of each rod element have a plurality of holes along the length of the central tube.

45. The system of claim 42 wherein the high surface area material comprises activated carbon, and the central backing rod comprises a metal or graphite material.

46. A fluid separator system for the electrical separation of a fluid containing separable components, which system comprises:

a) a housing having an inlet for the introduction of a fluid to be separated and an outlet for the withdrawal of separated components or reduced component fluid;

b) a flow-through electrical capacitor disposed in the housing, the capacitor comprising:

i) a microporous first high surface area electrically-conductive three-dimensional carbon-containing material layer to act as a stationary phase anode;

ii) a microporous second high surface area electrically-conductive material three-dimensional carbon-containing layer to act as a stationary phase cathode;

iii) a spacer material layer between the anode and cathode to define a fluid flow channel to permit the fluid to contact the anode and cathode;

iv) the first and second high surface area electrically-conductive material layers disposed to face each other externally on either side of the spacer material; and v) electrical lead means from the anode and from the cathode; and c) a direct current power source connected to the electrical lead means to supply electrical power to the anode and cathode to provide for the adsorption-desorption of selected components of the fluid by the first or second high surface area material layers.

47. The system of claim 46 wherein the first and second electrically conductive material layers comprise azite.

48. The system of claim 46 wherein the spacer material layer comprises a non-porous spacer material.

49. The system of claim 46 which includes a plurality of alternating anodes and cathodes and wherein the electrical lead means are integrally formed and extend from the first and second carbon-containing material layers.

50. The system of claim 46 wherein the first and second carbon-containing material layers are selected from the group consisting of spiral module layers, stacked disc layers and rod layers.

* * * * *